(12) United States Patent
Hasegawa (10) Patent No.: US 12,277,708 B2
(45) Date of Patent: Apr. 15, 2025

(54) ULTRASONIC DIAGNOSIS APPARATUS FOR DISPLAYING ULTRASOUND IMAGE WITH RESPECT TO LIVING BODY AND IMAGE PROCESSING METHOD

(71) Applicant: FUJIFILM Healthcare Corporation, Kashiwa (JP)

(72) Inventor: Ryota Hasegawa, Chiba (JP)

(73) Assignee: FUJIFILM Corporation, Tokyo (JP)

( * ) Notice: Subject to any disclaimer, the term of this patent is extended or adjusted under 35 U.S.C. 154(b) by 395 days.

(21) Appl. No.: 17/829,622

(22) Filed: Jun. 1, 2022

(65) Prior Publication Data

US 2022/0398734 A1    Dec. 15, 2022

(30) Foreign Application Priority Data

Jun. 11, 2021  (JP) ................................ 2021-098065

(51) Int. Cl.

| | |
|---|---|
| *G06T 7/00* | (2017.01) |
| *A61B 8/00* | (2006.01) |
| *G06T 5/20* | (2006.01) |
| *G06T 5/70* | (2024.01) |
| *G06T 7/11* | (2017.01) |
| *G06V 10/75* | (2022.01) |
| *G06T 3/4076* | (2024.01) |

(52) U.S. Cl.
CPC .......... *G06T 7/0014* (2013.01); *A61B 8/5269* (2013.01); *G06T 5/20* (2013.01); *G06T 5/70* (2024.01); *G06T 7/11* (2017.01); *G06V 10/751* (2022.01); *G06T 3/4076* (2013.01); *G06T 2207/10132* (2013.01); *G06T 2207/20016* (2013.01); *G06T 2207/20192* (2013.01); *G06T 2207/30104* (2013.01)

(58) Field of Classification Search
None
See application file for complete search history.

(56) References Cited

U.S. PATENT DOCUMENTS 8,068,700 B2 * 11/2011 Tsunekawa ........... G06T 3/4007
382/284
2005/0237544 A1 * 10/2005 Suzuki .................. G06T 3/4015
358/525

(Continued)

FOREIGN PATENT DOCUMENTS

| JP | 2009-153918 | 7/2009 |
|---|---|---|
| JP | 2012-050816 A | 3/2012 |

(Continued)

OTHER PUBLICATIONS

Feb. 6, 2024 Japanese official action (machine translation into English) in connection with Japanese Patent Application No. 2021-098065.

*Primary Examiner* — Haris Sabah
(74) *Attorney, Agent, or Firm* — Paul Teng (57) ABSTRACT

In a target image generated by multi-resolution processing, a pixel of interest and a group of reference pixels are designated. In a corresponding image belonging to a level that is one level above, pixel value patterns are compared between a corresponding region of interest and corresponding reference regions so as to calculate weights. A modified pixel-of-interest value is determined by means of multiplying the reference pixel values by the weights.

16 Claims, 6 Drawing Sheets

(56) References Cited

U.S. PATENT DOCUMENTS

| | | | | |
|---|---|---|---|---|
| 2012/0035478 A1* | 2/2012 | Nishihara | ........... | G01S 7/52074 |
| | | | | 600/443 |
| 2014/0118578 A1* | 5/2014 | Sasaki | ...................... | G06T 5/20 |
| | | | | 348/241 |
| 2017/0100100 A1 | 4/2017 | Jamello et al. | | |
| 2019/0325215 A1* | 10/2019 | Wang | ................... | G06T 7/0012 |

FOREIGN PATENT DOCUMENTS

| | | |
|---|---|---|
| JP | 2013-013436 | 1/2013 |
| JP | 2013-150778 | 8/2013 |
| JP | 2014-064736 | 4/2014 |
| JP | 2017-209329 | 11/2017 |
| JP | 2019-126524 | 8/2019 |
| WO | WO2017/062264 A1 | 4/2017 |

* cited by examiner

ULTRASONIC DIAGNOSIS APPARATUS FOR DISPLAYING ULTRASOUND IMAGE WITH RESPECT TO LIVING BODY AND IMAGE PROCESSING METHOD

CROSS REFERENCE TO RELATED APPLICATION

This application claims priority to Japanese Patent Application No. 2021-098065 filed on Jun. 11, 2021, which is incorporated herein by reference in its entirety including the specification, claims, drawings, and abstract.

TECHNICAL FIELD

The present disclosure relates to an ultrasonic diagnosis apparatus and an image processing method, and more particularly to a technique for improving image quality of ultrasound images.

BACKGROUND

An ultrasonic diagnosis apparatus is an apparatus configured to form and display an ultrasound image based on data obtained by performing ultrasound transmission and reception with respect to a living body. As the ultrasound image, a tomographic image, a blood flow image, and the like are known.

An ultrasound image contains speckle noise, which is inherent noise. In order to improve image quality of an ultrasound image, it is necessary to reduce speckle noise. If a general smoothing filter is applied to an ultrasound image to reduce speckle noise, edges in the ultrasound image become blurred.

As a technique for reducing speckle noise while preserving the edges, multi-resolution processing is known (for example, refer to JP 2009-153918 A and JP 2014-64736 A). In this processing, the resolution of an input image is reduced stepwise to thereby generate level input images corresponding to a plurality of levels. Filter processing is applied to each of the level input images. The resolution of each of the respective images after the filter processing is increased, and then an output image is generated. Conventional multi-resolution processing does not employ pattern comparison.

The present disclosure is directed to, in ultrasound image processing, reducing speckle noise while preserving edges that show a form or structure of a tissue. Alternatively, the present disclosure is directed to achieving multi-resolution processing that employs pattern comparison.

SUMMARY

An ultrasonic diagnosis apparatus according to an aspect of the present disclosure includes: a transform unit configured to stepwise reduce the resolution of an input image and thereby generate level input images to be supplied to a plurality of levels; filters configured to function in the plurality of levels; and an inverse transform unit configured to, for the purpose of generating an output image corresponding to the input image, increase the resolutions of level output images generated in the plurality of levels. At least one of the filters includes: a calculator configured to designate, in a corresponding image that corresponds to a target image input into the filter and that belongs to a level that is one level above the level to which the filter belongs, a corresponding region of interest corresponding to a pixel of interest in the target image, as well as corresponding reference regions corresponding to reference pixels in the target image, and further configured to calculate weights by comparing a pixel value pattern in the corresponding region of interest with pixel value patterns in the respective corresponding reference regions; and a modifier configured to modify a pixel-of-interest value possessed by the pixel of interest by means of causing the weights to act on reference pixel values possessed by the reference pixels.

An image processing method according to an aspect of the present disclosure includes: a step of stepwise reducing the resolution of an input image generated by performing ultrasound transmission and reception, and thereby generating level input images to be supplied to a plurality of levels; and a step of increasing resolutions of level output images generated in the plurality of levels. Filter processing is performed in at least one of the plurality of levels. In the filter processing, in a corresponding image that corresponds to a target image input for the filter processing and that belongs to a level that is one level above the level to which the filter processing belongs, there is designated a corresponding region of interest corresponding to a pixel of interest in the target image, as well as corresponding reference regions corresponding to reference pixels in the target image. Further, weights are calculated by comparing a pixel value pattern in the corresponding region of interest with pixel value patterns in the respective corresponding reference regions, and a pixel-of-interest value possessed by the pixel of interest is modified by means of subjecting reference pixel values possessed by the reference pixels to weighted summation based on the weights.

BRIEF DESCRIPTION OF DRAWINGS

Embodiment(s) of the present disclosure will be described based on the following figures, wherein.

DESCRIPTION OF EMBODIMENTS

Embodiments will now be described by reference to the drawings.

(1) Overview of Embodiments

An ultrasonic diagnosis apparatus according to an embodiment comprises a transform unit, filters, and an inverse transform unit. The transform unit stepwise reduces the resolution of an input image and thereby generates level input images to be supplied to a plurality of levels. The filters function in the plurality of levels. For the purpose of generating an output image corresponding to the input image, the inverse transform unit increases the resolution of level output images generated in the plurality of levels. At least one of the filters includes a calculator and a modifier. In a corresponding image that corresponds to a target image input into the filter and that belongs to a level that is one level above the level to which the filter belongs, the calculator designates a corresponding region of interest corresponding to a pixel of interest in the target image, as well as corresponding reference regions corresponding to reference pixels in the target image, and calculates weights by comparing a pixel value pattern in the corresponding region of interest with pixel value patterns in the respective corresponding reference regions. The modifier modifies a pixel-of-interest value possessed by the pixel of interest by means of causing the weights to act on reference pixel values possessed by the reference pixels. The transform unit is equivalent to a transformer. The inverse transform unit is equivalent to an inverse transformer.

In general, a structure (i.e., a living tissue) in an ultrasound image has its inherent pixel value pattern (or pixel value distribution), and two parts in the same structure have similar pixel value patterns. In contrast, randomness is recognized in a pixel value pattern of speckle noise. Based on such difference in properties, the above-described configuration serves to modify the pixel-of-interest value by performing pixel value pattern comparison. According to the above-described configuration, speckle noise can be effectively reduced while preserving the edges. In the above-described configuration, in calculating the weights to be used in the filter, reference is made to the corresponding image belonging to a level that is one level above the level to which the filter belongs, instead of the target image input into the filter. Since the resolution of the corresponding image is higher than the resolution of the target image, pattern comparison can be performed with higher accuracy, and therefore a more appropriate set of weights can be calculated. If a region for pattern comparison were to be defined in the target image, the minimum size of the region would be limited by the resolution of the target image. When a region for pattern comparison is to be defined in the corresponding image, a smaller region can be defined.

As the above-noted filter, a non-local means filter may be used. By designating, in the target image, a group of reference pixels within a local region including the pixel of interest, and further designating, in the corresponding image, respective corresponding reference regions near the corresponding region of interest, it is possible to prevent information distant from the pixel of interest from being reflected in the pixel of interest.

As the transform unit, a plurality of downsamplers may be provided, or other transformers may be provided. As the inverse transform unit, a plurality of upsamplers may be provided, or other transformers may be provided. In an embodiment, the pixel of interest is included in the group of reference pixels. In other words, the group of reference pixels is composed of the pixel of interest and a plurality of nearby pixels.

In an embodiment, the region occupied by the reference pixels in the target image has a first size. Each of the corresponding region of interest and the corresponding reference regions has a second size. The second size is equivalent to a third size in the level to which the filter belongs. The third size is smaller than the first size. According to this feature, the size of each of the regions used for the pixel value pattern comparison is reduced based on the premise that the pixel value pattern comparison is performed in the corresponding image having a high resolution. The weights to be applied to the reference pixel values may be calculated by interpolating between weights generated by performing the comparison of the corresponding region of interest with the corresponding reference regions.

In an embodiment, the reference pixels are $p \times p$ number of pixels. Each of the corresponding region of interest and the corresponding reference regions is composed of $q \times q$ number of pixels. p and q are the same integer of 3 or greater. With this arrangement, calculation can be facilitated. In an embodiment, a weight is calculated for each direction as viewed from the pixel of interest, and each of the weights is applied to a nearby pixel value present in its corresponding direction.

In an embodiment, the plurality of levels include an nth level (where n is an integer of 2 or greater), which is the lowermost level. The filters include an nth-level filter that functions in the nth level. Into the nth-level filter, an nth-level input image is input as the target image.

In an embodiment, the plurality of levels further include an (n−1)th level. The filters further include an (n−1)th-level filter that functions in the (n−1)th level. Into the (n−1)th-level filter, an (n−1)th-level intermediate image generated in the (n−1)th level is input as the target image.

In an embodiment, the (n−1)th-level intermediate image is an image generated by summing an (n−1)th-level high-frequency component image contained in an (n−1)th-level input image and an (n−1)th-level low-frequency component image generated from an nth-level output image.

In an embodiment, into the (n−1)th-level filter, an (n−2)th-level intermediate image generated in an (n−2)th level is input as the corresponding image. The (n−2)th-level intermediate image is an image generated by summing an (n−2)th-level high-frequency component image contained in an (n−2)th-level input image and an (n−2)th-level low-frequency component image generated from an (n−1)th-level intermediate image.

In an embodiment, into the (n−1)th-level filter, the (n−2)th-level low-frequency component image generated from the (n−1)th-level intermediate image is input as the corresponding image. According to this arrangement, the corresponding image can be generated easily.

An image processing method according to an embodiment comprises a transform step and an inverse transform step. In the transform step, the resolution of an input image generated by performing ultrasound transmission and reception is reduced stepwise, and level input images to be supplied to a plurality of levels are thereby generated. In the inverse transform step, the resolution of level output images generated in the plurality of levels is increased. Filter processing is performed in at least one of the plurality of levels. In the filter processing, in a corresponding image that corresponds to a target image input for the filter processing and that belongs to a level that is one level above the level to which the filter processing belongs, a corresponding region of interest corresponding to a pixel of interest in the target image is designated, along with corresponding reference regions corresponding to reference pixels in the target image. Further, weights are calculated by comparing a pixel value pattern in the corresponding region of interest with pixel value patterns in the respective corresponding reference regions, and a pixel-of-interest value possessed by the pixel of interest is modified by means of subjecting reference pixel values possessed by the reference pixels to weighted summation based on the weights.

The above-described image processing method can be implemented with software functions. In that case, a program configured to execute the above-described image processing method is installed in an information processing device via a network or a portable storage medium. The concept of the information processing device covers an ultrasonic diagnosis apparatus, an ultrasonic diagnosis system, a computer, and the like. The above-noted program is stored in a non-transitory storage medium inside the information processing device.

(2) Details of Embodiments

Figure 1:
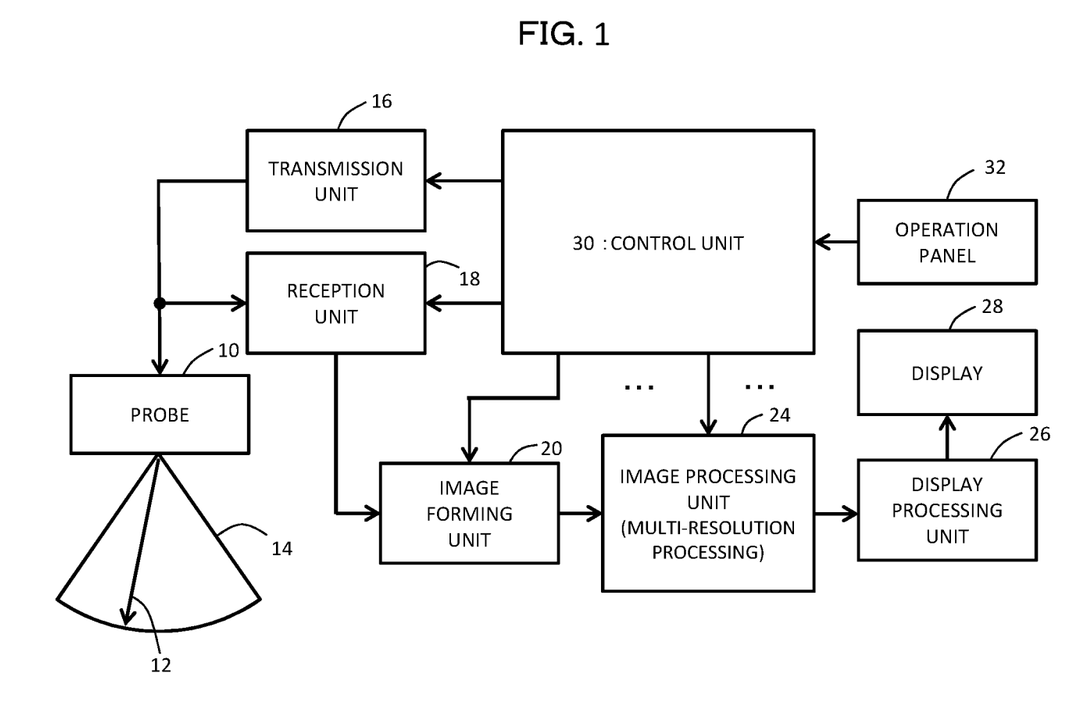
FIG. 1 is a block diagram showing a configuration of an ultrasonic diagnosis apparatus according to an embodiment.

FIG. 1 shows a configuration of an ultrasonic diagnosis apparatus according to an embodiment. The ultrasonic diagnosis apparatus is a medical apparatus configured to be installed in a medical institution or the like and to generate and display an ultrasound image based on data obtained by performing ultrasound transmission and reception with respect to an examinee's body (i.e., a living body).

In FIG. 1, a probe 10 is a portable ultrasound transmitter-receiver to be abutted against a surface of an examinee's body. Inside the probe 10, a transducer array composed of a plurality of transducers is provided. An ultrasound beam 12 is formed by the transducer array, and the ultrasound beam 12 is electronically scanned. As a result, a beam scan plane 14 is formed inside the examinee's body. The electronic scan of the ultrasound beam 12 is repeated to repeatedly form the beam scan plane 14. The beam scan plane 14 is a two-dimensional data capture region. As electronic scan methods, an electronic linear scan method, an electronic sector scan method, and the like are known. A two-dimensional transducer array may be provided in the probe 10 to obtain volume data from a three-dimensional space inside a living body.

A transmission unit 16 is a transmission circuit that functions as a transmission beamformer. A reception unit 18 is a reception circuit that functions as a reception beamformer. At the time of transmission, the transmission unit 16 outputs a plurality of transmission signals in parallel to the transducer array, and a transmission beam is thereby formed. At the time of reception, when reflected waves from the interior of a living body are received by the transducer array, a plurality of reception signals are output in parallel from the transducer array to the reception unit 18.

The reception unit 18 applies phase alignment and summation (i.e., delay and summation) processing to the reception signals and thereby forms sets of beam data. In accordance with the repeated electronic scans of the ultrasound beam 12, the reception unit 18 outputs a reception frame data array. One set of reception frame data is output per one electronic scan of the ultrasound beam 12. One set of reception frame data is constituted of a plurality of sets of beam data arranged serially along the electronic scan direction. One set of beam data is constituted of a plurality of sets of echo data arranged serially along the depth direction. At a stage after the reception unit 18, a beam data processing unit for processing the sets of beam data is provided, although it is not shown in the drawings. The beam data processing unit comprises an envelope detector, a logarithmic converter, and the like.

An image forming unit 20 serves to generate a display frame data array from a reception frame data array. The image forming unit 20 includes a DSC (digital scan converter). The DSC functions as a coordinate conversion unit. In other words, in the DSC, sets of data according to the transmission-reception ultrasound coordinate system are converted into sets of data according to the display coordinate system. Each of sets of display frame data constituting the display frame data array may be, for example, B-mode tomographic image data. Other types of ultrasound image data may be generated in the image forming unit 20.

An image processing unit 24 serves to apply multi-resolution processing for reducing speckle noise to the respective sets of display frame data constituting the display frame data array. Details of the multi-resolution processing are further described below by reference to FIG. 2 and subsequent figures. A processed display frame data array is output from the image processing unit 24 and input into a display processing unit 26. The multi-resolution processing for reducing speckle noise may be applied to the reception frame data array.

The display processing unit 26 has an image synthesis function, a color calculation function, and the like. In the display processing unit 26, images to be displayed on a display 28 are generated. Those images include, in the present embodiment, tomographic images in the form of a moving image. According to the present embodiment, since speckle noise is reduced in the image processing unit 24, high-quality tomographic images can be displayed on the display 28. The display 28 is composed of an LCD, an organic EL device, or the like.

A control unit 30 is composed of a CPU that executes programs. The control unit 30 controls operation of the respective constituent elements shown in FIG. 1. An operation panel 32 is connected to the control unit 30. The operation panel 32 is an input device comprising buttons, knobs, a trackball, a keyboard, and the like.

The image forming unit 20, the image processing unit 24, and the display processing unit 26 are respectively composed of processors that execute programs. Functions exhibited by those processors may alternatively be implemented by the above-noted CPU.

Figure 2:
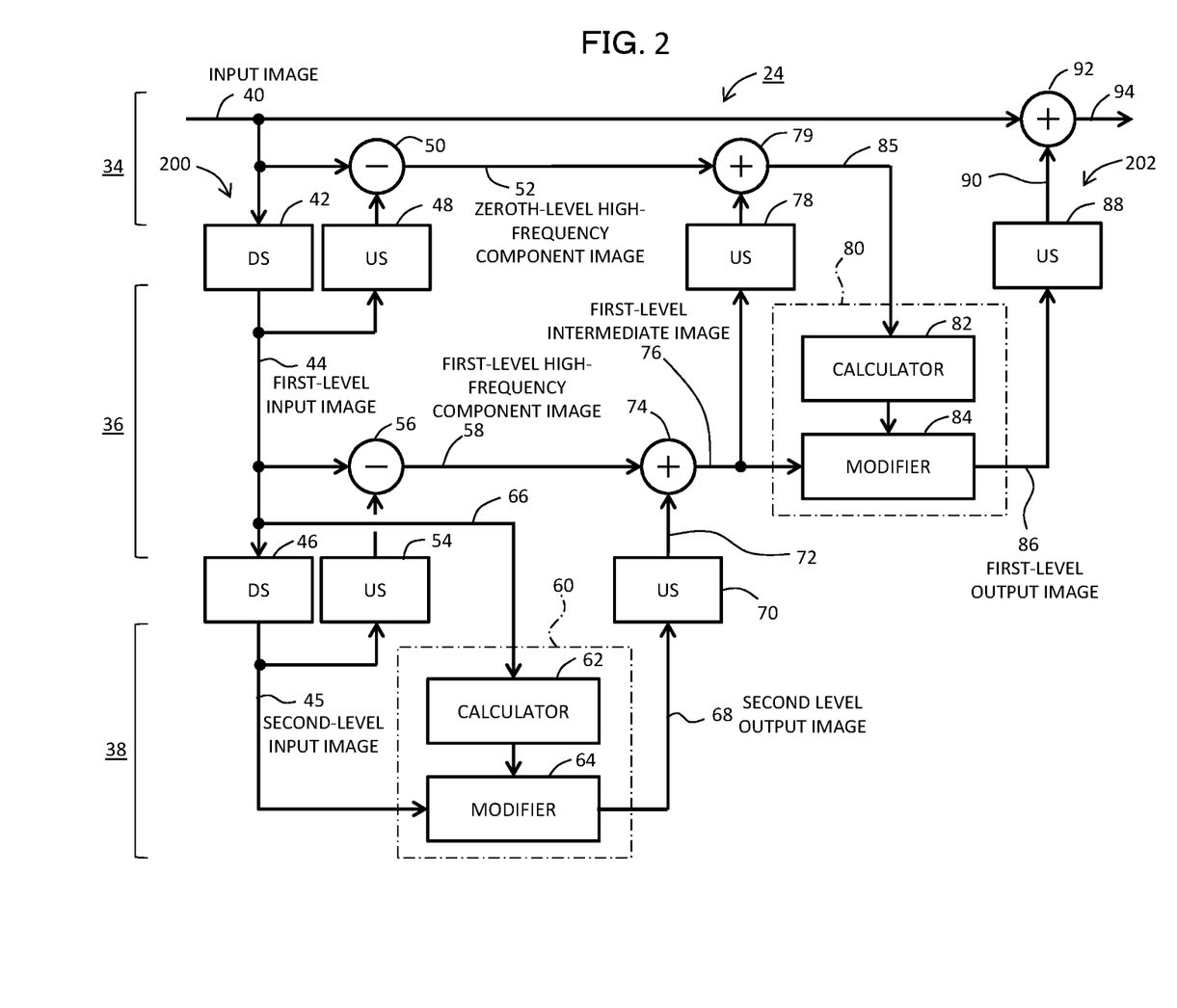
FIG. 2 is a diagram showing a first example configuration of an image processing unit.

FIG. 2 shows a first example configuration of the image processing unit 24. In the first example configuration, the first level to the nth level are shown. Here, n is typically an integer of 2 or greater, and in the example shown, n=2. The nth level is the lowermost level. The respective constituent elements shown in FIG. 2 can be implemented with software functions.

Reference numeral 34 denotes the zeroth level, to which an input image 40 belongs. Reference numeral 36 denotes the first level, which is one level lower than the zeroth level 34. Reference numeral 38 denotes the second level, which is one level lower than the first level 36. By stepwise reducing the resolution of the input image 40, a plurality of low-resolution images to be supplied to the plurality of levels 36, 38 are generated.

Tomographic images (or sets of reception frame data) constitute the input image 40. To each tomographic image, the image processing for reducing speckle noise is applied. Ultrasound images other than tomographic images may be processed in the image processing unit 24. A transform unit 200 serves to stepwise reduce the resolution of the input image 40, and is composed of a plurality of downsamplers (DS) 42, 46.

An inverse transform unit 202 serves to increase the resolution of output images 68, 86 generated in the plurality of levels 36, 38, and is composed of a plurality of upsamplers (US) 70, 88. Other than those USs 70 and 88, USs 48, 54, and 78 are also provided.

In the DS 42, the input image is downsampled to generate a first-level input image 44. During the downsampling, every other one of the pixels (i.e., pixel values) sequentially arranged along the x-direction (i.e., horizontal direction) is removed for thinning, and every other one of the pixels (i.e., pixel values) sequentially arranged along the y-direction (i.e., vertical direction) is removed for thinning. Each of the x-direction thinning rate and the y-direction thinning rate is ½. The first-level input image 44 is equivalent to an image downsized to ¼ relative to the input image 40.

The DS 46 serves to exert the same effect as the DS 42. In the DS 46, the first-level input image 44 is downsampled to generate a second-level input image 45. The second-level input image 45 is equivalent to an image downsized to ¹⁄₁₆ relative to the input image 40.

In actual practice, before performing the downsampling, each of the DSs 42, 46 executes Gaussian processing (i.e., convolution of a Gaussian weighting factor matrix) with respect to an image that serves as the processing target. On the other hand, each of the USs 48, 54, 70, 78, 88 executes, after upsampling, Gaussian processing with respect to an image serving as the processing target.

A filter 60 serves to apply filter processing to the second-level input image 45. Specifically, each of the pixels constituting the second-level input image 45 is designated as a pixel of interest, and a group of reference pixels is defined with the pixel of interest located at the center. In the present embodiment, the pixel of interest is also included in the group of reference pixels. By performing weighted summation of pixel values of the reference pixels constituting the group of reference pixels, a modified pixel-of-interest value for the pixel of interest is determined. The filter 60 includes a calculator 62 for calculating a set of weights, and a modifier 64 for executing the weighted summation using the set of weights.

In the present embodiment, the calculator 62 calculates a set of weights based on the first-level input image 44 belonging to the first level 36, which is one level above the second level, instead of based on the second-level input image 45 belonging to the second level 38 (see reference numeral 66).

From the viewpoint of the filter 60, the second-level input image 45 is the target image, and the first-level input image 44 is the corresponding image corresponding to the target image. Each of the pixels constituting the target image is designated as a pixel of interest, and in the target image, a group of reference pixels is designated with the pixel of interest located at the center. Meanwhile, in the corresponding image, a corresponding region of interest having, at the center, a corresponding pixel of interest that corresponds to the pixel of interest is designated, and also a plurality of corresponding reference regions having, at their centers, respective corresponding reference pixels that correspond to the reference pixels are designated. Pixel value pattern comparison is performed between the corresponding region of interest and the corresponding reference regions, and based on degrees of similarity obtained as a result, weights are determined. From the filter 60, the second-level output image 68 is output as the processed image.

The US 54 upsamples the second-level input image 45 to generate a first-level low-frequency component image. A subtractor 56 subtracts the first-level low-frequency component image from the first-level input image 44 to thereby generate a first-level high-frequency component image 58. Meanwhile, the US 70 upsamples the second-level output image 68 to generate a processed first-level low-frequency component image 72. An adder 74 sums the first-level high-frequency component image 58 and the processed first-level low-frequency component image 72 to thereby generate a first-level intermediate image 76.

A filter 80 belonging to the first level 36 has the same configuration as the above-noted filter 60, and serves to exert the same effect as the above-noted filter 60. The filter 80 includes a calculator 82 and a modifier 84. The target image that serves as the processing target for the filter 80 is the first-level intermediate image 76. The calculator 82 generates a set of weights, and in doing so, refers to a corresponding image corresponding to the target image.

The corresponding image is a high-resolution image belonging to the zeroth level (see reference numeral 85). The modifier 84 calculates a modified pixel-of-interest value for each pixel of interest by performing weighted summation using the set of weights calculated by the calculator 82.

The US 48 upsamples the first-level input image 44 to generate a zeroth-level low-frequency component image. A subtractor 50 subtracts the zeroth-level low-frequency component image from the input image (i.e., zeroth-level input image) 40 to thereby generate a zeroth-level high-frequency component image 52. Meanwhile, the US 78 upsamples the first-level intermediate image 76 to generate a processed zeroth-level low-frequency component image. An adder 79 adds the processed zeroth-level low-frequency component image to the zeroth-level high-frequency component image 52 to thereby generate a zeroth-level intermediate image. This zeroth-level intermediate image is used as the corresponding image (see reference numeral 85).

As explained earlier, a corresponding region of interest and corresponding reference regions are designated in the corresponding image, and by performing pixel value pattern comparison between these regions, a set of weights is calculated. In the first example configuration, the corresponding image supplied to the filter 80 is an image generated in a level that is one level above, and this point is the same as the corresponding image supplied to the filter 60.

From the filter 80, the first-level output image 86 is output as the processed image. The US 88 upsamples the first-level output image 86. An adder 92 sums the input image 40 and an upsampled image 90 to thereby generate an output image 94. In the adder 92, weighted summation is performed. Here, two weights to be applied to the two images are either set fixedly or set adaptively.

Figure 3:
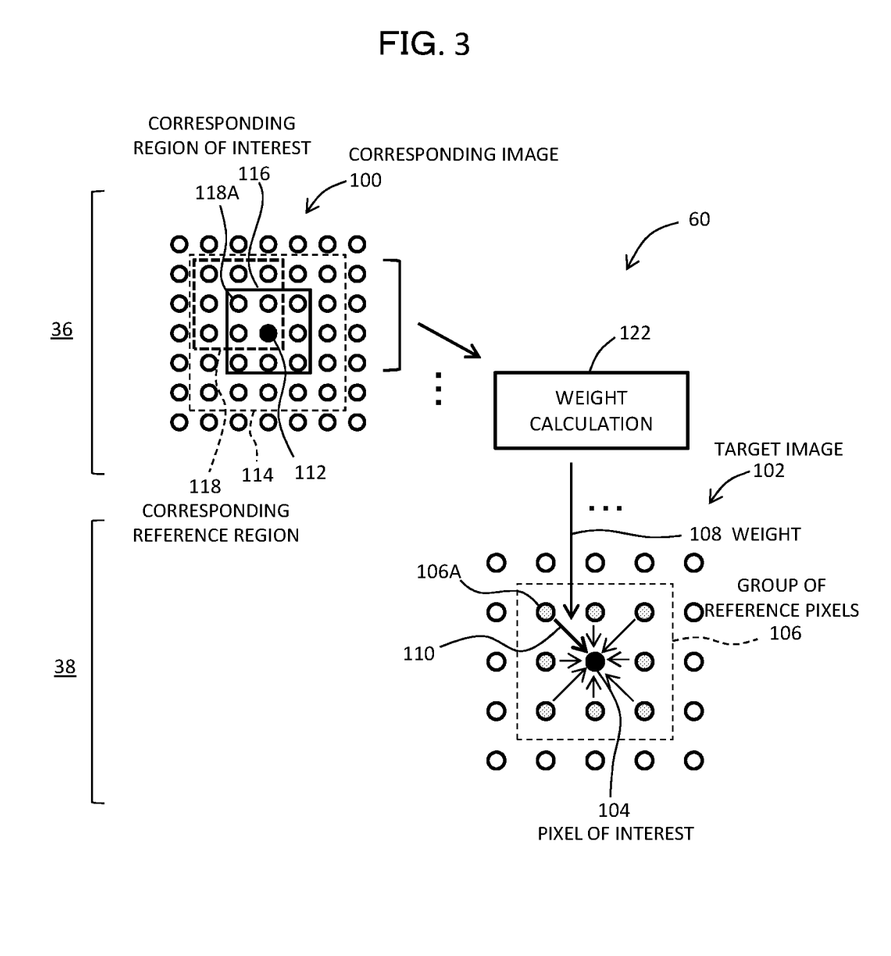
FIG. 3 is a diagram showing weighted summation processing.

FIG. 3 schematically illustrates processing performed in the filter 60. In the second level 38, each of the pixels constituting the target image 102 is designated as a pixel of interest 104. Further, a group of reference pixels 106 including p×p number of pixels with the pixel of interest 104 located at the center is designated. In the example shown, p=3. p may be an integer of 4 or greater (typically an odd number). The group of reference pixels 106 is composed of the pixel of interest 104 and eight nearby pixels located near the pixel of interest. By summing products obtained by multiplying the values of the reference pixels by weights, a modified pixel value for the pixel of interest 104 is determined.

In calculating the weights, a corresponding image 100 belonging to the first level 36, which is one level above the second level 38, is used. Specifically, in the corresponding image 100, a corresponding pixel of interest 112 corresponding to a pixel of interest is designated as a base point, and with this base point located at the center, a corresponding region of interest 116 for pattern comparison is set. In addition, in the corresponding image 100, corresponding reference pixels 118A corresponding to reference pixels are designated, and with these respective corresponding reference pixels located at the centers, corresponding reference regions 118 are set. The corresponding reference regions 118 are designated within a defined region 114 having the corresponding pixel of interest 112 located at the center. Each of the regions 114, 116, 118 is also referred to as a kernel.

In the present embodiment, each of the corresponding region of interest 116 and the corresponding reference regions 118 is composed of q×q number of pixels. In the present embodiment, q=3; that is, q=p.

When the size of the region occupied by the reference pixels 106 is expressed as a first size, and the size of each of the corresponding region of interest 116 and the corresponding reference regions 118 is expressed as a second size, the second size is equivalent to a third size in the second level 38, and the third size is smaller than the first size. In the present embodiment, small kernels that cannot be designated in the target image 102 can be designated by referring to the image belonging to a level that is one level above.

Pixel value pattern comparison is performed between the corresponding region of interest 116 and the nine corresponding reference regions, and nine degrees of similarity are thereby obtained. The nine degrees of similarity may be employed without any change as nine weights, or nine weights may be calculated from the nine degrees of similarity. The weight calculation is denoted in FIG. 3 by reference numeral 122. For example, when a reference pixel 106A and the corresponding reference pixel 118A are in a relationship of correspondence, the pixel value (typically the luminance value) possessed by the reference pixel 106A is multiplied by a weight 108 calculated between the corresponding region of interest 116 having the corresponding pixel of interest 112 at the center and the corresponding reference region 118 having the corresponding reference pixel 118A at the center. This weighted pixel value is reflected in the modified pixel-of-interest value of the pixel of interest 104 (see reference numeral 110). This processing is carried out with respect to all of the reference pixels, and the modified pixel-of-interest value is determined as a weighted sum. The foregoing processing is applied to every pixel constituting the target image 102. The second-level output image is thus generated.

In general, in an ultrasound image, a structure in a living body has its inherent pixel value pattern. On the other hand, a pixel value pattern of speckle noise lacks uniformity. According to the above-described processing, speckle noise can be effectively reduced while preserving the edges. Furthermore, since an image belonging to a level that is one level above is referred to in calculating a set of weights, pattern comparison can be performed with a higher accuracy.

In real space, the position of the pixel of interest 104 basically coincides with the position of the corresponding pixel of interest 112, or the two positions are in a relationship of close similarity. The positions of the respective reference pixels do not coincide with the positions of the respective corresponding reference pixels, but the directions as viewed from the pixel of interest in which the reference pixels are located coincide with the directions as viewed from the corresponding pixel of interest in which the corresponding reference pixels are located. The technique according to the present embodiment can be described as equivalent to weight calculations for respective directions.

For example, in performing the filter processing, weights w(i, j) are calculated according to the following formulas (1-1) and (1-2).

$$w(i,j)=1/Z(i)\exp(-\Sigma_{m=-M/2}^{M/2}(x(i+m)-x(j+m))^2/h^2) \quad (1\text{-}1)$$

$$Z(i)=\Sigma_{j=i-N/2}^{i+N/2}\exp(-\Sigma_{m=-M/2}^{M/2}(x(i+m)-x(j+m))^2/h^2) \quad (1\text{-}2)$$

Here, i is the coordinate of the pixel of interest, and j is the coordinate of the reference pixel. x(i) is the luminance value of the pixel of interest, and w(i, j) is the weight by which x(j) is to be multiplied. Z(i) is a normalization coefficient. N denotes the size of the entire region referred to in calculating the weights (where N is an odd number), and M denotes the size of the corresponding region of interest and the corresponding reference regions (where M is an odd number). h is a smoothing parameter. Using the weights w(i, j) calculated as above, the luminance value y(i) of the pixel of interest after the filter processing is calculated according to the following formula (2).

$$y(i)=\Sigma_{j=i-N/2}^{i+N/2}x(j)*w(i,j) \quad (2)$$

In place of the above formulas (1-1) and (1-2), the following formulas (3-1) and (3-2) may alternatively be used to calculate the weights w(i, j).

$$w(i,j)=1/Z(i)\exp(-\Sigma_{m=-M/2}^{M/2}\text{MAX}((x(i+m)-x(j+m))^2-2h^2,0)/h^2) \quad (3\text{-}1)$$

$$Z(i)=\Sigma_{j=i-N/2}^{i+N/2}\exp(-\Sigma_{m=-M/2}^{M/2}\text{MAX}((x(+m)-x(j+m))^2-2h^2,0)/h^2) \quad (3\text{-}2)$$

The calculation formulas noted above are shown simply by way of example. Other calculation formulas may be used to calculate the weights and the modified luminance value.

Figure 4:
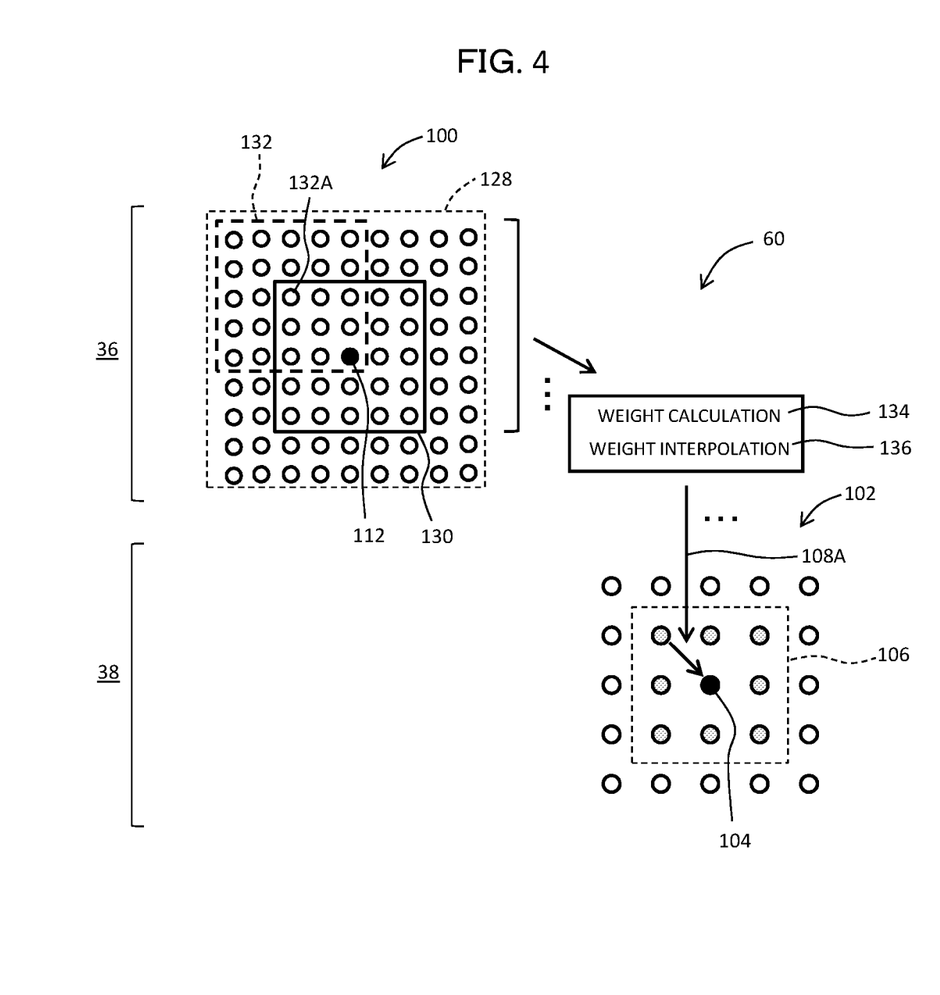
FIG. 4 is a diagram showing a variant of the weighted summation processing.

FIG. 4 shows a variant of the processing performed in the filter 60. Elements in FIG. 4 that are identical to those shown in FIG. 3 are labeled with the same reference numerals, and description thereof will not be repeated.

As explained above, the pixel of interest 104 and the group of reference pixels 106 are designated in the target image 102. The group of reference pixels 106 is composed of p×p number of reference pixels, where p is 3.

Meanwhile, in the corresponding image 100, a corresponding region of interest composed of q×q number of pixels with a corresponding pixel of interest 112 located at the center is designated, where p<q<2×p, and for example, q=5. A region 128 defined as a sum of corresponding reference regions 132 is composed of 9×9 pixels, but this region 128 may alternatively be composed of 7×7 pixels.

Weights are calculated between the corresponding region of interest 130 and the respective corresponding reference regions 132 (see reference numeral 134). By performing interpolation processing based on the weights (or set of weights) calculated between the corresponding region of interest 130 and the corresponding reference regions 132, an interpolation value 108A is calculated as the weight for each reference pixel (see reference numeral 136), and the reference pixel value is multiplied by this interpolation value 108A. Here, in calculating the set of weights between the corresponding region of interest 130 and the corresponding reference regions 132, calculation of those weights that are not to be referred to for the interpolation processing may be omitted. The filter processing conditions including the value of p, the value of q, and the like may be set by the user or set automatically in accordance with the nature and the processing purpose of the input image.

Figure 5:
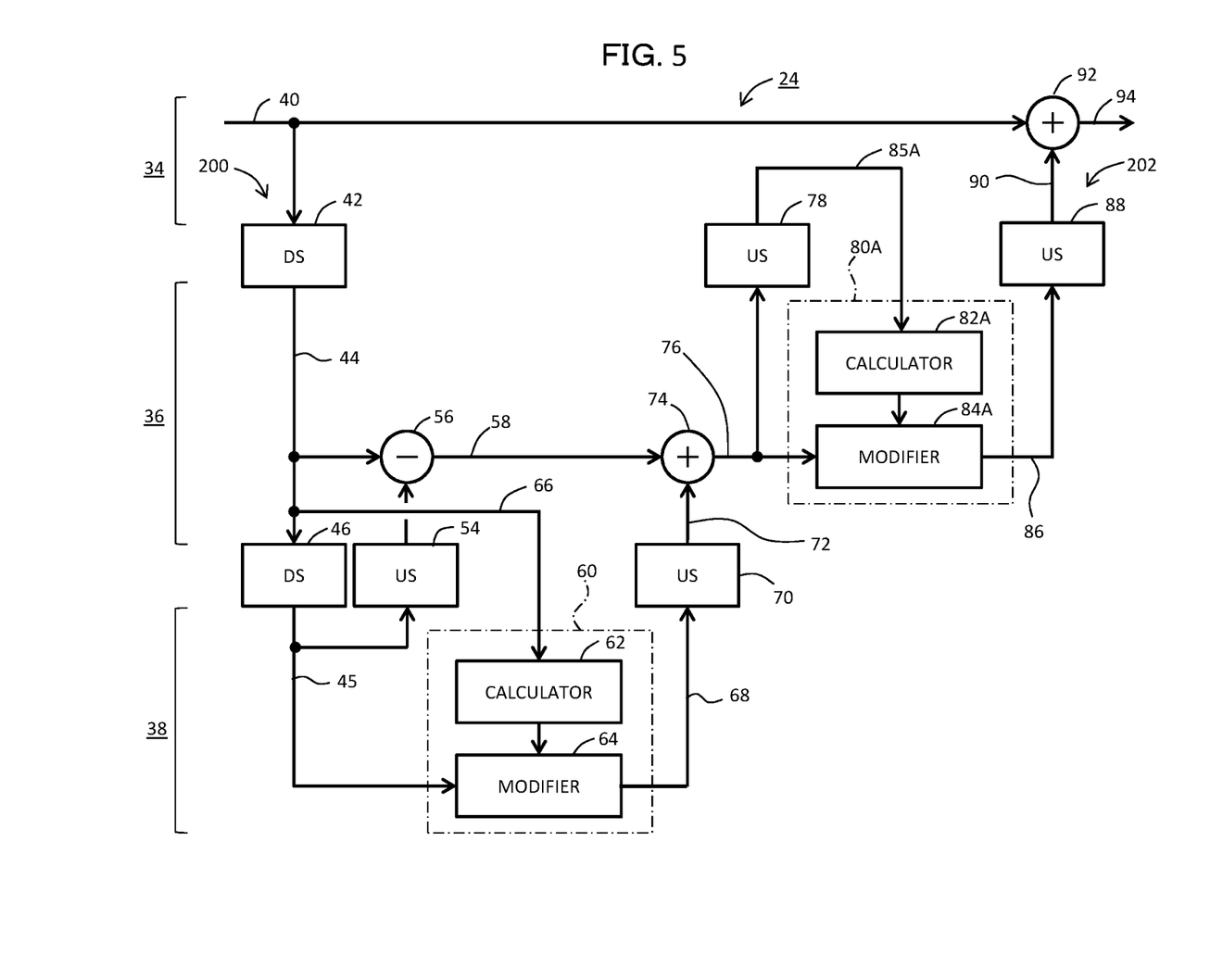
FIG. 5 is a diagram showing a second example configuration of the image processing unit.

FIG. 5 shows a second example configuration of the image processing unit. Elements in FIG. 5 that are identical to those shown in FIG. 2 are labeled with the same reference numerals, and description thereof will not be repeated. This applies similarly to a third example configuration shown in FIG. 6.

In the second example configuration shown in FIG. 5, the input image for the filter 80A is the first-level intermediate image 76, and this point is no different from the first example configuration. However, in the second example configuration, the upsampled image output from the US 78 is input as is into the filter 80A belonging to the first level 36 (see reference numeral 85A). In terms of resolution, this image is an image belonging to the zeroth level, and this point is the same as in the first example configuration. According to the second example configuration, the corresponding image referred to by the filter 80A can be generated easily, and the configuration can be simplified to that extent. On the other hand, in cases where the first example configuration shown in FIG. 2 is employed, it is possible to achieve the advantage that pixel value pattern comparison can be performed with a higher accuracy; i.e., the likelihood of computing a more appropriate set of weights can be increased.

Figure 6:
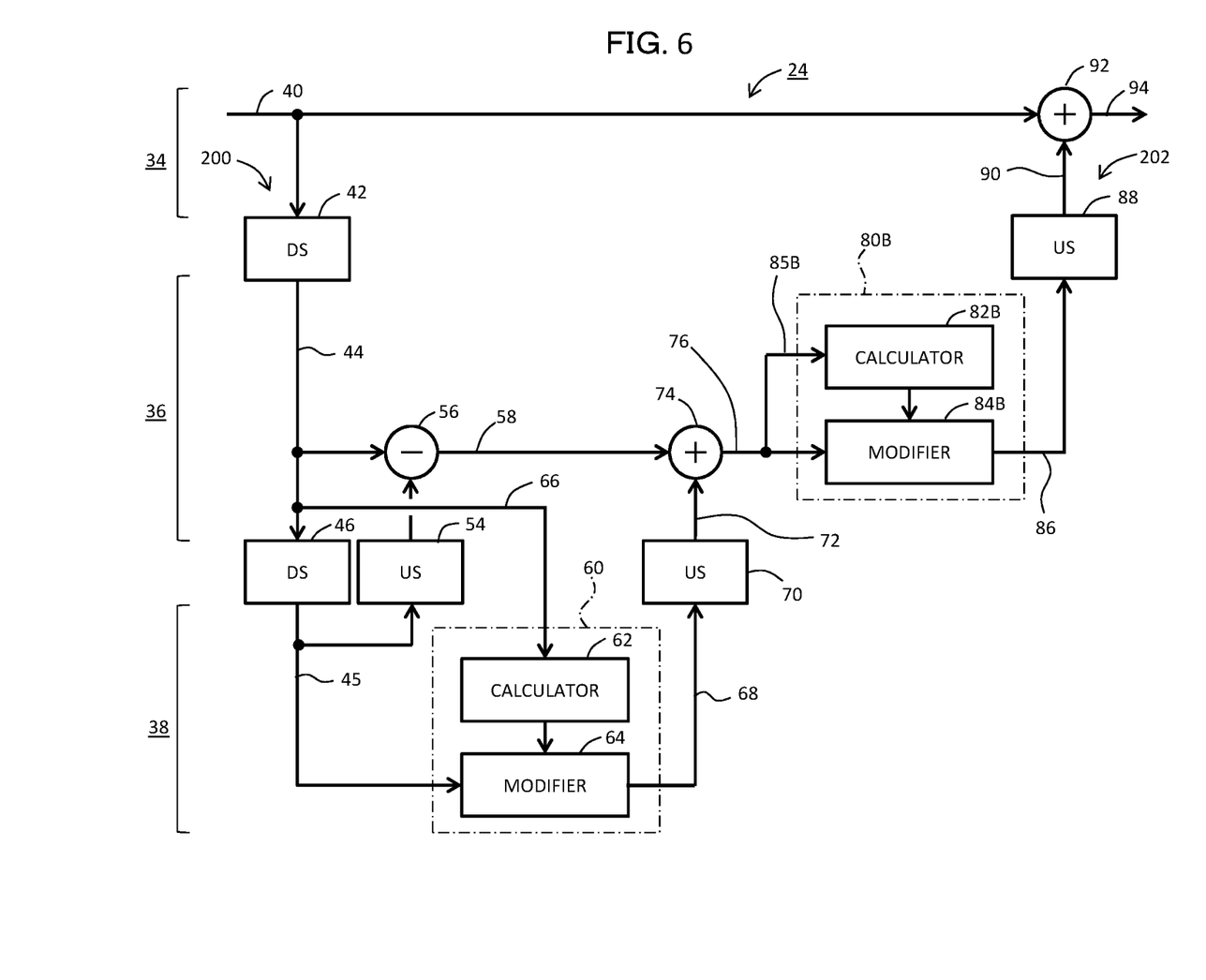
FIG. 6 is a diagram showing a third example configuration of the image processing unit.

FIG. 6 shows a third example configuration of the image processing unit. As the target image for a filter 80B belonging to the first level, the first-level intermediate image 76 is input, and this point is no different from the first and the second example configurations. However, in the third example configuration, the corresponding image referred to by the filter 80B is also the first-level intermediate image 76 (see reference numeral 85B). In the third example configuration, the configuration of the first level 36 can be further simplified. In the filter 60 belonging to the second level 38, a first-level input image belonging to a level that is one level above is referred to as the corresponding image as in the first and the second example configurations, so that, in connection with the filter processing in the second level 38, the above-described advantages can be obtained. The third example configuration may be employed when it is desired to increase the accuracy of filter processing of low-frequency components as compared to that of high-frequency components while also simplifying the configuration.

In general, speckle noise includes various frequency components, so that the multi-resolution processing with respect to speckle noise is effective. During the multi-resolution processing, in performing the weighted summation based on pixel value pattern comparison for the filter processing belonging to each level, a more appropriate set of weights can be computed by referring to an image belonging to a level that is one level above. Further, since the area referred to can be limited to a local area, it is possible to prevent or reduce instances in which information at locations distant from the pixel of interest is reflected in the pixel of interest.

Techniques other than downsampling and upsampling may be used in carrying out the resolution conversions. For example, wavelet transform or the like may be used. In each of the levels, a plural number of times of filter processing may be applied to the target image.

The invention claimed is:

1. An ultrasonic diagnosis apparatus configured to generate an ultrasound image based on data obtained by performing ultrasound transmission and reception with respect to a living body, the ultrasonic diagnosis apparatus comprising:
   a reception unit configured to receive reception signals corresponding to an input image; and
   an image processing unit configured to apply processing for reducing speckle noise in the input image, the image processing unit including:
      a transform unit configured to stepwise reduce a resolution of the input image and generate level input images to be supplied to a plurality of levels;
      filters configured to perform filter processing in the plurality of levels; and
      an inverse transformer configured to increase resolutions of level output images generated in the plurality of levels and to generate an output image corresponding to the input image,
   wherein at least one filter among the filters is configured to include:
      a calculator configured to designate, in a corresponding image that corresponds to a target image input into the filter and that belongs to a level that is one level above a level to which the filter belongs, a corresponding region of interest corresponding to a pixel of interest in the target image, as well as corresponding reference regions corresponding to reference pixels in the target image, and further configured to calculate weights by comparing a pixel value pattern in the corresponding region of interest with pixel value patterns in the respective corresponding reference regions; and
      a modifier configured to output a processed image by modifying a pixel-of-interest value possessed by the pixel of interest and applying the weights to act on reference pixel values possessed by the reference pixels.

2. The ultrasonic diagnosis apparatus according to claim 1, wherein
   a region occupied by the reference pixels in the target image has a first size;
   each of the corresponding region of interest and the corresponding reference regions has a second size;
   the second size is equivalent to a third size in the level to which the filter belongs; and
   the third size is smaller than the first size.

3. The ultrasonic diagnosis apparatus according to claim 1, wherein
   the reference pixels are p×p number of pixels;
   each of the corresponding region of interest and the corresponding reference regions is composed of q×q number of pixels; and
   p and q are the same integer of 3 or greater.

4. The ultrasonic diagnosis apparatus according to claim 1, wherein
   the plurality of levels include an nth level (where n is an integer of 2 or greater), which is a lowermost level;
   the filters include an nth-level filter that functions in the nth level; and
   into the nth-level filter, an nth-level input image is input as the target image.

5. The ultrasonic diagnosis apparatus according to claim 4, wherein
   the plurality of levels further include an (n−1)th level;
   the filters further include an (n−1)th-level filter that functions in the (n−1)th level; and
   into the (n−1)th-level filter, an (n−1)th-level intermediate image generated in the (n−1)th level is input as the target image.

6. The ultrasonic diagnosis apparatus according to claim 5, wherein
   the (n−1)th-level intermediate image is an image generated by summing an (n−1)th-level high-frequency component image contained in an (n−1)th-level input image and an (n−1)th-level low-frequency component image generated from an nth-level output image.

7. The ultrasonic diagnosis apparatus according to claim 5, wherein
   into the (n−1)th-level filter, an (n−2)th-level intermediate image generated in an (n−2)th level is input as the corresponding image; and
   the (n−2)th-level intermediate image is an image generated by summing an (n−2)th-level high-frequency component image contained in an (n−2)th-level input image and an (n−2)th-level low-frequency component image generated from the (n−1)th-level intermediate image.

8. The ultrasonic diagnosis apparatus according to claim 5, wherein into the (n−1)th-level filter, an (n−2)th-level low-frequency component image generated from the (n−1)th-level intermediate image is input as the corresponding image.

9. An image processing method performed by an ultrasonic diagnosis apparatus, comprising:

stepwise reducing a resolution of an input image generated by the ultrasonic diagnosis apparatus performing ultrasound transmission and reception, and generating level input images to be supplied to a plurality of levels;

performing filter processing, in at least one level of the plurality of levels, the filter processing comprising in a corresponding image that corresponds to a target image input for the filter processing and that belongs to a level that is one level above a level to which the filter processing belongs, designating a corresponding region of interest corresponding to a pixel of interest in the target image, as well as corresponding reference regions corresponding to reference pixels in the target image, calculating weights by comparing a pixel value pattern in the corresponding region of interest with pixel value patterns in the respective corresponding reference regions, and outputting a processed image including modifying a pixel-of-interest value possessed by the pixel of interest and subjecting reference pixel values possessed by the reference pixels to weighted summation based on the weights; and increasing resolutions of level output images generated in the plurality of levels and generating an output image corresponding to the input image.

10. The image processing method according to claim 9, wherein a region occupied by the reference pixels in the target image has a first size, each of the corresponding region of interest and the corresponding reference regions has a second size that is equivalent to a third size in the level to which the filter belongs, and the third size is smaller than the first size.

11. The image processing method according to claim 9, wherein the reference pixels are p×p number of pixels, each of the corresponding region of interest and the corresponding reference regions is composed of q×q number of pixels, and p and q are the same integer of 3 or greater.

12. The image processing method according to claim 9, wherein the plurality of levels include an nth level (where n is an integer of 2 or greater), which is a lowermost level, the filters include an nth-level filter that is in the nth level, and into the nth-level filter, an nth-level input image is input as the target image.

13. The image processing method according to claim 12, wherein the plurality of levels further include an (n−1)th level, the filters further include an (n−1)th-level filter that is in the (n−1)th level, and into the (n−1)th-level filter, an (n−1)th-level intermediate image generated in the (n−1)th level is input as the target image.

14. The image processing method according to claim 13, wherein the (n−1)th-level intermediate image is an image generated by summing an (n−1)th-level high-frequency component image contained in an (n−1)th-level input image and an (n−1)th-level low-frequency component image generated from an nth-level output image.

15. The image processing method according to claim 13, wherein into the (n−1)th-level filter, an (n−2)th-level intermediate image generated in an (n−2)th level is input as the corresponding image, and the (n−2)th-level intermediate image is an image generated by summing an (n−2)th-level high-frequency component image contained in an (n−2)th-level input image and an (n−2)th-level low-frequency component image generated from the (n−1)th-level intermediate image.

16. The image processing method according to claim 13, wherein into the (n−1)th-level filter, an (n−2)th-level low-frequency component image generated from the (n−1)th-level intermediate image is input as the corresponding image.

* * * * *